(12) United States Patent
Zarychta

(10) Patent No.: US 6,411,843 B1
(45) Date of Patent: Jun. 25, 2002

(54) METHOD AND APPARATUS FOR PRODUCING A MODEL EMG SIGNAL FROM A MEASURED EMG SIGNAL

(75) Inventor: Jaroslaw Zarychta, Winnipeg (CA)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/567,795

(22) Filed: May 9, 2000

Related U.S. Application Data

(60) Provisional application No. 60/136,551, filed on May 28, 1999.

(51) Int. Cl.⁷ ................................................. A61B 5/04
(52) U.S. Cl. .................................. 600/546; 128/204.23
(58) Field of Search ....................... 128/203.14, 204.23; 600/546, 513

(56) References Cited

U.S. PATENT DOCUMENTS

| | | | |
|---|---|---|---|
| 4,155,353 A | 5/1979 | Rea et al. | |
| 4,170,225 A | 10/1979 | Criglar et al. | |
| 4,209,860 A | 7/1980 | Graupe | |
| 4,213,466 A | 7/1980 | Stulen | |
| 4,913,146 A | 4/1990 | DeCote, Jr. | |
| 4,964,411 A | 10/1990 | Johnson et al. | |
| 5,003,976 A | 4/1991 | Alt | |
| 5,016,635 A | 5/1991 | Graupe | |
| 5,058,602 A | 10/1991 | Brody | |
| 5,277,197 A | 1/1994 | Church et al. | |
| 5,318,039 A | 6/1994 | Kadefors et al. | |
| 5,374,193 A | 12/1994 | Trachtman | |
| 5,579,781 A | 12/1996 | Cooke | |
| 5,645,073 A | 7/1997 | Kadefors et al. | |
| 5,671,752 A | 9/1997 | Sinderby et al. | |
| 5,697,378 A | 12/1997 | Elghazzawi | |
| 5,711,307 A | 1/1998 | Smits | |
| 5,820,560 A | * 10/1998 | Sinderby et al. | ............ 600/546 |

* cited by examiner

Primary Examiner—Jeffrey R. Jastrzab
(74) Attorney, Agent, or Firm—Michael W. Haas

(57) ABSTRACT

A model EMG signal is produced from a measured EMG signal that includes a patient's EMG signal and ECG signal by processing the measured EMG signal to produce a logic signal that is in a first binary state in the absence of a P wave, a QRS complex and a T wave of an ECG cycle of the measured EMG signal and that is in a second binary state during at least one of the P wave, the QRS complex and the T wave of the ECG cycle. The measured EMG signal is processed to produce a first envelope signal. The model EMG signal is produced as a function of the first envelope signal when the logic signal is in the first binary state and the absence of the first envelope signal when the logic signal is in the second binary state.

36 Claims, 7 Drawing Sheets

METHOD AND APPARATUS FOR PRODUCING A MODEL EMG SIGNAL FROM A MEASURED EMG SIGNAL

CROSS REFERENCE TO RELATED APPLICATION

This application claims priority under 35 U.S.C. § 119(e) from U.S. Provisional Patent Application No. 60/136,551 filed May 28, 1999.

BACKGROUND OF THE INVENTION

1. Field of the Invention

This invention relates to detection of an EMG signal and, more particularly, to a method and apparatus that produces a model diaphragm EMG signal, which can be utilized, for example, to monitor the condition of a patient and/or synchronize the operation of a ventilator to the breathing cycle of a patient.

2. Description of the Related Art

Ventilators used to promote the exchange of air in the lungs of a patient are well-known in the art. Ventilators operate by urging air into the lungs of the patient during inhalation and by terminating urging air into the patient's lungs during exhalation. In a normal patient, the inhalation and exhalation of air into and out of the lungs are accomplished by activation and relaxation of the patient's respiratory muscles, and, in particular, the diaphragm muscles, which contract and relax in response to a signal from the phrenic nerve. The activation of the diaphragm produces an electromyographic (EMG) signal and, more particularly, a diaphragm EMG signal, that can be measured. This diaphragm EMG signal is generally representative of the respiratory effort generated by the patient during each breath cycle.

The diaphragm EMG signal can be used for a variety of purposes, from monitoring the respiratory function of the patient to controlling a ventilator that assists the patient in breathing. For example, in general, some conventional ventilators operate on the principle that each inhalation by a patient has the same interval. Accordingly, if the interval of the patient's diaphragm EMG signal during inhalation is longer or shorter than the inhalation interval of the ventilator, the ventilator will provide to the patient more or less air, respectively, than the patient desires, with corresponding patient discomfort.

Conventional ventilators have attempted to utilize a measured EMG signal, and, in particular, the measured diaphragm EMG signal to control the supply of air or other breathing gas to the lungs of the patient. However, because the measured EMG signal contains the patient's diaphragm EMG signal, an electrocardiogram (ECG) signal, and other noise, such as noise due to movement between sensing electrodes and tissue of the patient during breathing, difficulties are encountered in synchronizing the operation of the ventilator with the diaphragm EMG signal of the patient.

A variety of techniques has been utilized to suppress or eliminate the contribution of an ECG signal and noise from the measured EMG signal to obtain a model of the EMG signal, i.e., a "clean" EMG signal, such as a clean diaphragm EMG signal, which corresponds to the EMG signal that is produced directly by the diaphragm. One conventional technique for producing a clean diaphragm EMG signal includes clipping the top of the QRS complex of the measured EMG signal. However, this technique is unsatisfactory because it leaves the majority of the QRS complex and may introduce new artifact harmonics to the frequency spectrum. Another technique includes replacing, for the duration of each QRS complex of each ECG cycle, the measured EMG signal with the value of the measured EMG signal recorded immediately prior to that QRS complex. A problem with this technique is that it leaves the remainder of the ECG cycle, which includes most of the low frequency power. In another conventional technique, computerized processing is utilized to subtract an ECG signal obtained during relaxation from the measured EMG signal. A problem with this technique is that the ECG signal will vary with effort, due to changes in both heart rate and recording conditions, which introduces artifacts. In yet another technique, the EMG signal is sampled between one T wave and a subsequent QRS complex. Such recordings have been utilized in spectral analysis of human diaphragm EMG signals. A problem with this technique is that the measured EMG signal is not sampled between the Q wave and the T wave of each ECG cycle thereby omitting relevant information.

SUMMARY OF THE INVENTION

It is, therefore, an object of the present invention to provide a method and apparatus for separating a model EMG signal from a measured EMG signal that overcomes the shortcomings of conventional EMG detection/analysis techniques. The model EMG signal can be used to monitor the condition of the patient. In the case of a diaphragm EMG signal, the model diaphragm EMG signal can be utilized, for example, to synchronize the operation of a ventilator and the breathing cycles of a patient.

This object is achieved according to one embodiment of the present invention by providing a method of producing a model EMG signal from a measured EMG signal that includes a patient's EMG signal and an ECG signal. The method includes processing the measured EMG signal to produce a logic signal that is in a first binary state in the absence of a P wave, a QRS complex, and a T wave of an ECG cycle of the measured EMG signal and in a second binary state during at least one of the P wave, the QRS complex, and the T wave of the ECG cycle. The measured EMG signal is processed to produce a first envelope signal. The model EMG signal is produced as a function of (1) the first envelope signal when the logic signal is in the first binary state and (2) the absence of the first envelope signal when the logic signal is in the second binary state.

An exemplary embodiment of the present invention contemplates that processing the measured EMG signal to produce the logic signal includes processing the measured EMG signal to produce a second envelope signal, and processing the second envelope signal to produce a fast signal. An exemplary embodiment of the present invention also processes the second envelope signal to produce a first slow signal having a slew rate that is slower than the slew rate of the fast signal. The method of the present invention processes the fast signal and the first slow signal to produce the logic signal.

An exemplary embodiment of the present invention also contemplates that processing the measured EMG signal to produce the first envelope signal includes high pass filtering the measured EMG signal to produce a high pass signal and rectifying the high pass signal to produce a rectified signal. The rectified signal is low pass filtered to produce the first envelope signal.

Producing the model EMG signal includes, in one embodiment of the present invention, providing a moving average of the first envelope signal when the logic signal is in the first binary state, and providing, when the logic signal is in the second binary state, a set value that corresponds to a value of the moving average of the first envelope signal when the logic signal changes from the first binary state to the second binary state.

A further embodiment of the method for separating a model EMG signal from a measured EMG signal according to the principles of the present invention contemplates processing the second envelope signal to produce a second slow signal having a slew rate that is slower than the slew rate of the fast signal, and processing the fast signal, the first slow signal, and the second slow signal to produce the logic signal.

The present invention also contemplates that the step of producing the model EMG signal includes continuously processing the measured EMG signal to produce a third envelope signal. When the logic signal is in the first binary state, a moving average of the first envelope signal is preferably provided. When the logic signal is in the second binary state, a moving average of the third envelope signal is provided.

It is another object of the present invention to provide an apparatus for producing a model EMG signal from a measured EMG signal, which includes a patient's EMG signal and ECG signal, that does not suffer from the disadvantage of conventional EMG signal generating devices. This object is achieved according to the principles of the present invention by providing an apparatus that includes a logic signal processing means for processing the measured EMG signal to produce a logic signal that is in a first binary state in the absence of a P wave, a QRS complex, and a T wave of an ECG cycle of the measured EMG signal and in a second binary state during at least one of the P wave, the QRS complex, and the T wave of the ECG cycle. A first envelope processing means processes the measured EMG signal to produce a first envelope signal. An averaging means produces the model EMG signal as a function of (1) the first envelope signal when the logic signal is in the first binary state and (2) the absence of the first envelope signal when the logic signal is in the second binary state.

In an exemplary embodiment of the present invention, the logic signal processing means includes a second envelope processing means that processes the measured EMG signal to produce a second envelope signal. In addition, a fast signal processing means process the second envelope signal to produce a fast signal. A first slow signal processing means processes the second envelope signal to produce a first slow signal having a slew rate that is slower than the slew rate of the fast signal. A comparing means compares the fast signal and the first slow signal to produce the logic signal.

An exemplary embodiment of the present invention further contemplates that the first envelope processing means includes a high pass filtering means for high pass filtering the measured EMG signal to produce a first high pass signal. A rectifying means rectifies the first high pass signal to produce a rectified signal, and a low pass filtering means low pass filters the rectified signal to produce the first envelope signal.

The present invention also contemplates that second envelope processing means includes a first low pass filtering means for filtering the measured EMG signal to produce a first filtered signal. A first rectifying means rectifies the first filtered signal to produce the second envelope signal. The fast signal processing means includes a second low pass filtering means for filtering the second envelope signal to produce a second filtered signal. A first amplifying means amplifies the second filtered signal to produce a first amplified signal. A third low pass filtering means filters the first amplified signal to produce a third filtered signal and a combining means combines the second filtered signal and the third filtered signal to produce the fast signal.

An exemplary embodiment of the present invention further contemplates that the first slow signal processing means includes a second amplifying means for amplifying the second envelope signal to produce a second amplified signal. A fourth low pass filtering means low pass filters the second amplified signal to produce the first slow signal. The comparing means includes a first comparator means for comparing the fast signal and the first slow signal and which, as a function of comparison, produces the logic signal.

The apparatus further contemplates that a second slow signal processing means processes the second envelope signal to produce a second slow signal having a slew rate that is slower than the slew rate of the fast signal. The comparing means produces the logic signal as a function of the fast signal, the first slow signal and the second slow signal.

The present invention also contemplates that the second slow signal processing means includes the second amplifying means, which amplifies the second envelope signal, to produce the second amplified signal as well as a fifth low pass filtering means that low pass filters the second amplified signal to produce the second slow signal.

The comparing means include a first comparator means for comparing the fast signal and the first slow signal to produce a first comparator signal. A second comparator means compares the fast signal and the second slow signal to produce a second comparator signal. In addition, a logic gate means combines the first comparator signal and the second comparator signal to produce the logic signal.

The second slow signal processing means produces the second slow signal as a function of (1) the second envelope signal when the first comparator is in the first binary state and (2) when the first comparator is in the second binary state, a set value corresponding to the value of the second envelope signal when the first comparator changes from first binary state to the second binary state.

The present invention further contemplates that apparatus for producing a model EMG signal from a measured EMG signal includes a third envelope processing means for continuously processing the measured EMG signal to produce a third envelope signal. When the logic signal is in the first binary state, the averaging means produces a moving average of the first envelope signal, and when the logic signal is in the second binary state, the averaging means produces a moving average of the third envelope signal.

It is still another embodiment to provide an apparatus for producing a model EMG signal from a measured EMG signal that includes a patient's EMG signal and ECG signal. The apparatus includes a first envelope processor, which processes the measured EMG signal, to produce a first envelope signal. A second envelope processor processes the measured EMG signal to produce a second envelope signal. A fast signal processor processes the second envelope signal to produce a fast signal and a first slow signal processor processes the second envelope signal to produce a first slow signal. A comparer compares the fast signal and the first slow signal to produce a logic signal which is in a first binary state in the absence of a P wave, a QRS complex and a T wave of an ECG cycle of the measured EMG signal and which is in a second binary state during at least one of the P wave, the QRS complex and the T wave of the ECG cycle.

An averager produces a model EMG signal as a function of (1) the first envelope signal when the logic signal is the first binary state and (2) the absence of the first envelope signal when the logic signal is in the second binary state.

A first switch couples or isolates the measured EMG signal and the first envelope processor when the logic signal is in the first and second binary states, respectively. A second switch couples or isolates the first envelope signal and the averager when the logic signal is in the first and second binary states, respectively.

In a further embodiment, the apparatus includes a second slow signal processor that processes the second envelope signal to produce a second slow signal. The comparer also produces the logic signal as a function of the fast signal, the first slow signal and the second slow signal.

In a still further embodiment, a third envelope processor that continuously processes the measured EMG signal to produce a third envelope signal. The second switch couples the first envelope signal to the averager when the logic signal is in the first binary state and couples the third envelope signal to the averager when the logic signal is in the second binary state. The averager produces the model EMG signal as a function of the first envelope signal when the logic signal is in the first binary state and as a function of the third envelope signal when the logic signal is in the second binary state.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EXEMPLARY EMBODIMENTS OF THE INVENTION

Figure 1:
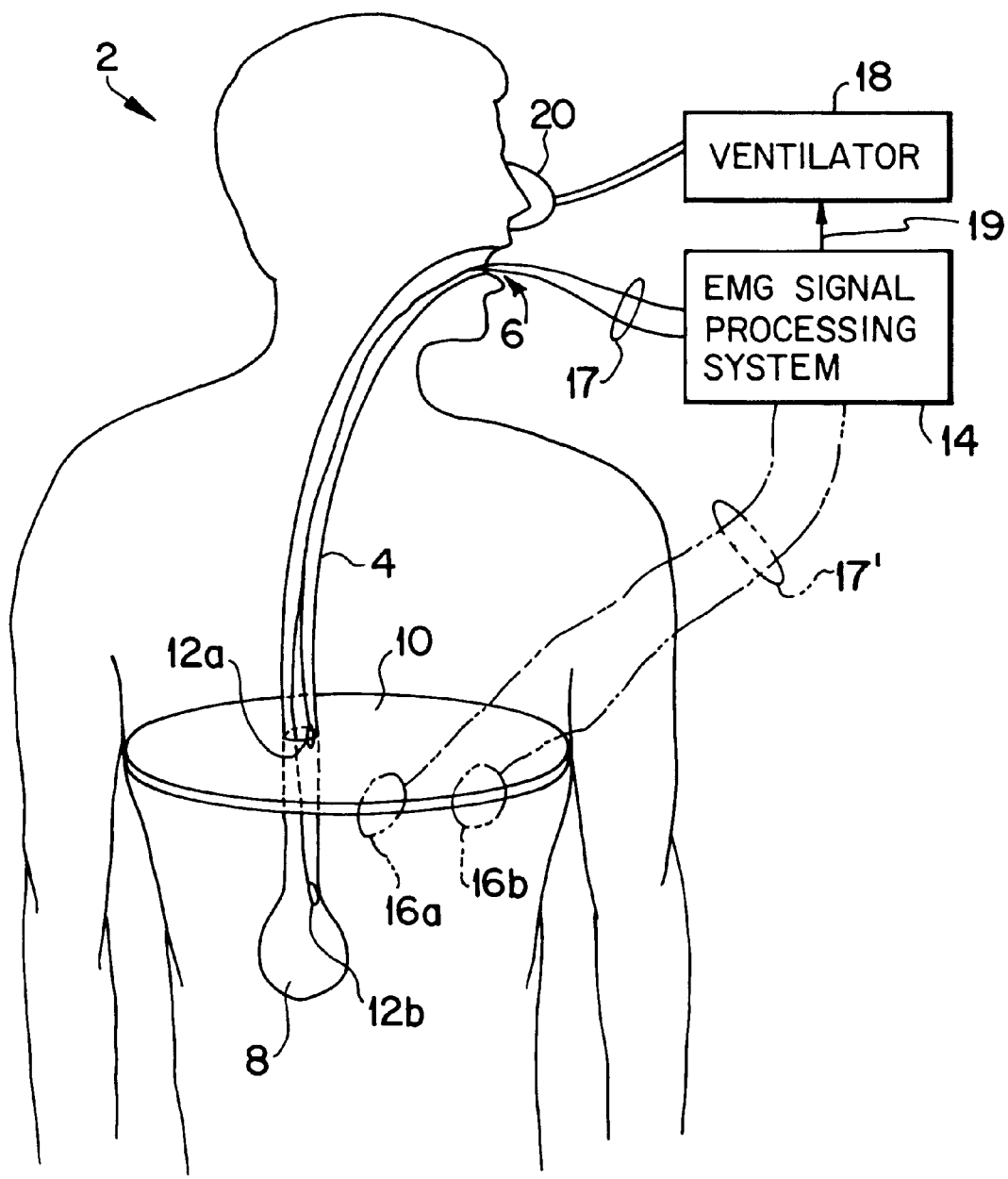
FIG. 1 is a schematic diagram illustrating an EMG signal processing system of the present invention connected between a patient and a ventilator.

The present invention will be described below with reference to FIGS. 1–7, As shown in FIG. 1, a normal human 2 has an esophagus 4 that extends between a mouth 6 and a stomach 8. A normal human also has a diaphragm 10 that is shown as a disk in FIG. 1 for simplicity of illustration. During normal breathing, diaphragm 10 receives from the nervous system of the patient, i.e., the phrenic nerve, a neural impulse that causes diaphragm 10 to contract and relax in a manner well known in the art. Contraction of the diaphragm can be detected by measuring the electromyographic (EMG) signals generated by the diaphragm during contraction.

To measure this EMG signal, electrodes 12a and 12b are preferably positioned in esophagus 4 with one electrode 12a placed very close to diaphragm 10 and the other electrode 12b placed away from the diaphragm. Electrodes 12a and 12b are connected to an EMG signal processing system 14 disposed outside patient 2. In an alternative configuration, electrodes 16a and 16b, which are shown in phantom in FIG. 1, are attached at or near the surface of the patient parallel and as close as possible to diaphragm 10 and connected to EMG signal processing system 14. In another alternative configuration, surface electrodes 16a and 16b are disposed on the patient such that one electrode is near the diaphragm and one electrode is spaced therefrom. In a normal human, electrodes 12a, 12b and 16a, 16b detect the EMG signal produced by diaphragm 10, as well as other electrical signals in the body, such as the patient's electrocardiogram (ECG) signal and noise. Such noise can include motion artifacts associated with the sensors and/or EMG signals from other muscles, e.g., the intercostal muscles. A measured EMG signal 17 from electrodes 12a and 12b are provided to EMG signal processing system 14. Similarly, a measured EMG signal 17' from electrodes 16a and 16b are provided to EMG signal processing system 14.

While the present invention illustrates measured EMG signals 17, 17' as being measured by electrode pairs 12a, 12b within the patient or by electrode pairs 16a, 16b outside the patient, it is to be understood that these configurations and locations are not exclusive. On the contrary, the present invention contemplates providing electrodes at any location on the patient so long as they detect the EMG signal of interest, such as the diaphragm EMG signal. For example, one electrode in the electrode pair can be provided within the patient and the other electrode in that pair provided can be outside the patient. It is to be understood, that due to human physiology, any electrodes provided in, on, or near the patient to detect the diaphragm EMG will also detect noise, most notably the patient's ECG signals, due the relatively close location of the heart and diaphragm in a normal patient.

Ventilator 18 is a device that supplies a breathing gas, such as air, to an airway of patient 2 during inhalation and controls release of air from patient 2 during exhalation. Patient interface device 20, such as a nasal and/or oral mask, trachea tube, or endotracheal tube, connects ventilator 18 with the patient's airway, such as the nose (as shown) and/or mouth. In the illustrated embodiment, patient interface device 20 is a mask provided around the nose and/or mouth of the patient to define a seal between against the patient so that breathing gas can be non-invasively delivered to the airway of the patient. While a non-invasive ventilation technique is specifically described above, it is to be understood that the present invention contemplates that ventilator can be any conventional ventilator that communicates with the airway of a patient using any conventional technique, such as the two-limb, pressure or volume, invasive ventilation systems that deliver breathing gas via a intubation tube or trachea tube.

Preferably, EMG signal processing system 14 receives measured EMG signal 17 from electrodes 12a,12b and/or 16a, 16b, generates, and supplies to ventilator 18 an amplified model diaphragm EMG signal 19 that corresponds to the diaphragm EMG signal received at diaphragm 10. In a preferred embodiment of the present invention, the amplified model diaphragm EMG signal 19 is used to synchronize the operation of ventilator with the patient's breathing cycle so that the application of an inspiratory pressure or flow by the ventilator is synchronized with the inspiratory effort of the patient, and likewise, the patient's expiration is synchronized to the expiratory cycle of the ventilator.

It is to be understood, however, that the present invention contemplates a variety of other uses for the model diaphragm EMG signal 19, in addition to or instead of using this signal to control a ventilator. Other uses for diaphragm EMG signal are well known to those skilled in the art, and include, for example, monitoring the patient pulmonary function and/or measuring physiological parameters. Information gathered from the diaphragm EMG signal or other EMG signals can be used to set the control or operating parameters for a medical device, such as a ventilator. The EMG signals can also be used to control the application of electrical stimulation to the upper airway muscles and/or nerves to treat obstructive sleep apnea. It is to be understood that the present invention is not limited to these uses for the EMG signals, and, in particular, the diaphragm EMG signal. Rather, the present invention is directed to the generation of a clean EMG signal from raw a EMG signal performed by the EMG signal processing system. Therefore, the present invention can be used in conjunction with any EMG signal and the resulting clean EMG signal can be used for any purpose. The use of a diaphragm EMG signal to control and/or augment the control of a ventilator is provided for the purpose of illustration.

Details of an exemplary embodiment of EMG signal processing system 14, that effectively separates amplified model diaphragm EMG signal 19 from measured EMG signal 17, 17' received from electrodes 12a, 12b and/or 16a, 16b, respectively, are discussed below with reference to FIG. 2. More specifically, EMG signal processing system 14 isolates a model diaphragm EMG signal 19 from measured EMG signal 17 that includes the patient's diaphragm EMG signal, ECG signal and noise.

Figure 2:
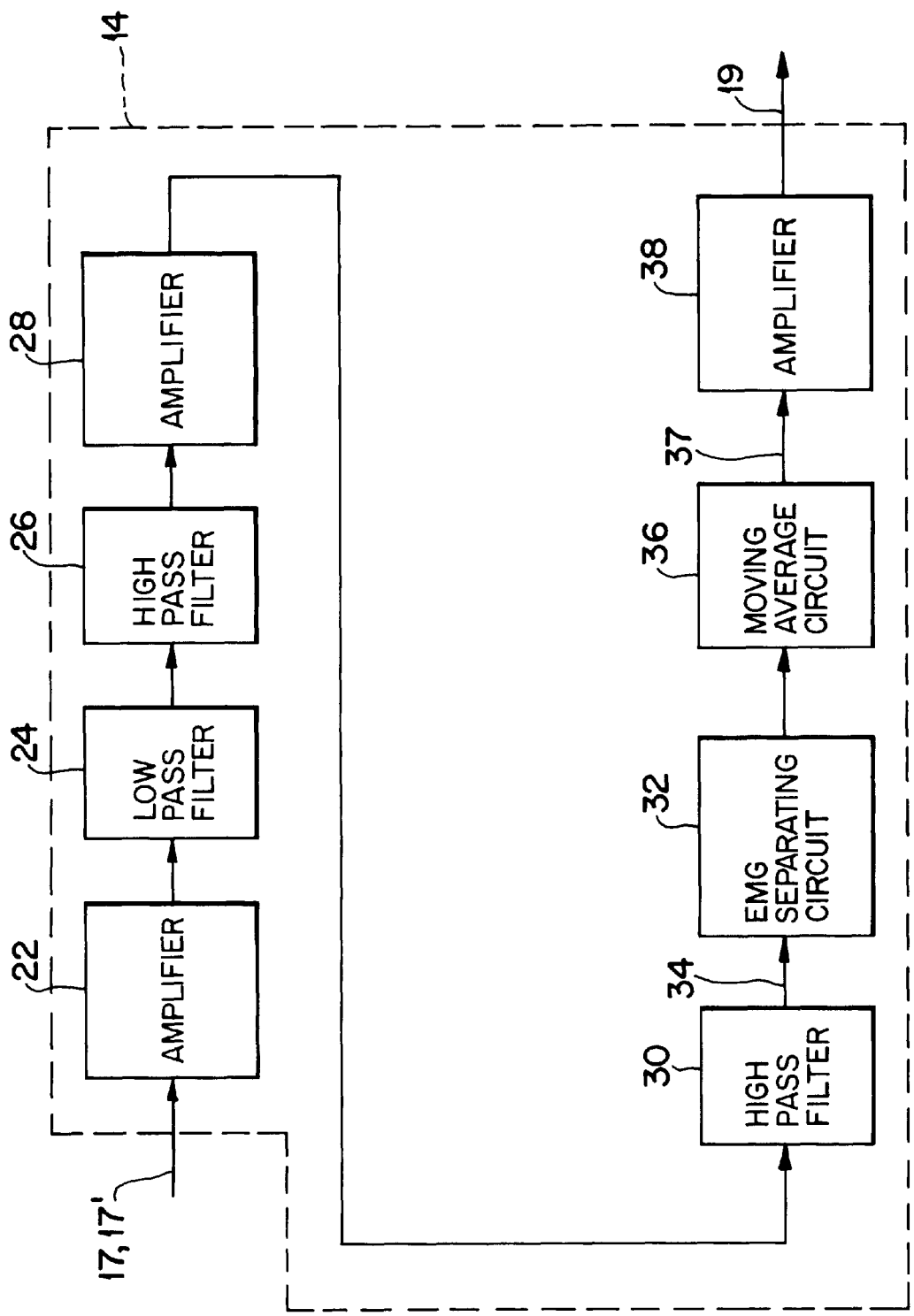
FIG. 2 is a schematic diagram illustrating in greater detail the EMG signal processing system shown in FIG. 1.

As shown in FIG. 2, EMG signal processing system 14 includes an amplifier 22 that receives the measured EMG signal 17, 17' from electrodes 12a, 12b and/or 16a, 16b and amplifies the measured EMG signal 17, 17'. Preferably, amplifier 22 has a gain of about 100. Amplifier 22 supplies an amplified EMG signal to a low pass filter 24. Low pass filter 24 filters the amplified EMG signal to produce a low pass filtered signal that is, in turn, supplied to a high pass filter 26. The low pass filter 24 preferably has a crossover frequency of about 1.6 kHz and an attenuation of about −12 db/octave. High pass filter 26 filters the low pass filtered signal from the low pass filter 24 and supplies to amplifier 28 a high pass filtered signal. Preferably, high pass filter 26 has a crossover frequency of about 0.1 Hz and an attenuation of about −12 db/octave. Low pass filter 24 and high pass filter 26 effectively form a band pass filter having a band pass frequency between about 0.1 Hz and 1.6 kHz. Thus, the present invention contemplates replacing the combination of low pass filter 24 and high pass filter 26 with a single band pass filter having similar pass bands.

Amplifier 28 amplifies the high pass filtered signal from high pass filter 26 and supplies the amplified high pass filtered signal to a high pass filter 30. Preferably, amplifier 28 has a gain of about 100. High pass filter 30 filters the amplified high pass filtered signal from amplifier 28 and supplies a processed EMG signal 34 to an EMG separating circuit 32. The details of EMG separating circuit 32 and how it operates on processed EMG signal 34 are discussed hereinafter. Preferably, high pass filter 30 has a crossover frequency of about 24 Hz and an attenuation of about −24 db/octave. EMG separating circuit 32, operating in combination with a moving average circuit 36, produce, from the processed EMG signal 34, a model diaphragm EMG signal 37, which is supplied to an amplifier 38. Moving average circuit 36 produces the model diaphragm EMG signal 37 as a function of a moving average of the signal received from the EMG separating circuit 32. Amplifier 38 amplifies model diaphragm EMG signal 37 to produce amplified model diaphragm EMG signal 19, which, according to one embodiment of the present invention, is supplied to ventilator 18. Model diaphragm EMG signal 37 and, hence, amplified model diaphragm EMG signal 19 are representations of the patient's diaphragm EMG signal. Preferably, amplifier 38 has a gain between about 1 and 10.

In the embodiment shown in FIG. 2, measured EMG signal 17, 17' is processed by amplifiers 22 and 28 and filters 24, 26 and 30 to produce processed EMG signal 34. It is to be understood, however, that the present invention contemplates providing measured EMG signal 17, 17' directly to the EMG separating circuit 32. In the ensuing description, EMG separating circuit 32 is described as receiving processed EMG signal 34. However, it should be understood that EMG separating circuit 32 can receive measured EMG signal 17, 17'. It can thus be appreciated that processed EMG signal 34 received by the EMG separating circuit 32 corresponds to measured EMG signal 17, 17' including the amplification and filtering provided by amplifiers 22 and 28 and filters 24, 26 and 30, respectively.

Figure 3:
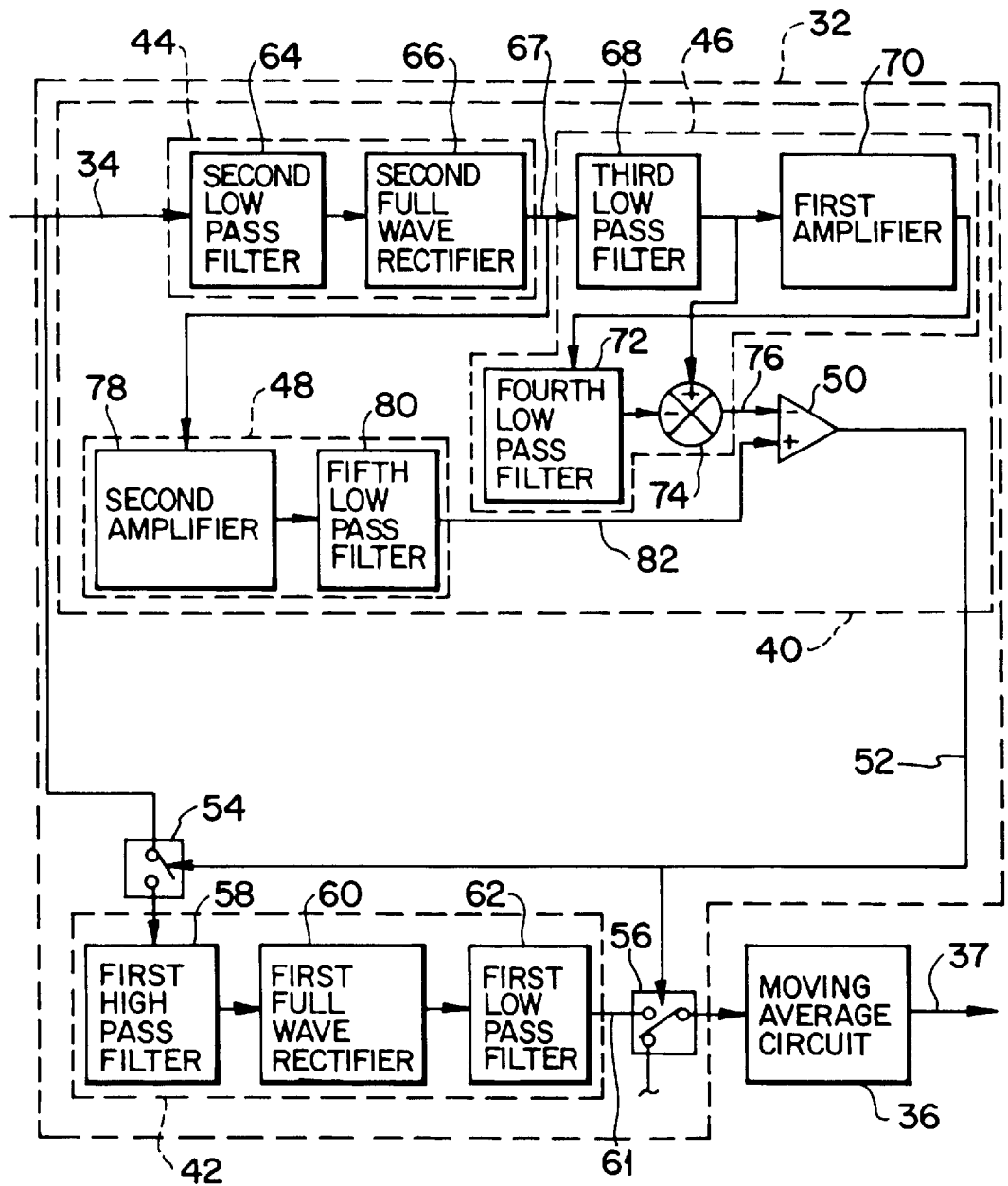
FIG. 3 is a schematic diagram of one embodiment of an EMG separating circuit of the EMG signal processing system shown in FIG. 2.

With reference to FIG. 3, and with continuing reference to FIGS. 1 and 2, one embodiment of EMG separating circuit 32 is described below. EMG separating circuit 32 includes a logic signal processor 40 and a first envelope processor 42. Logic signal processor 40 includes a second envelope processor 44, a fast signal processor 46, a first slow signal processor 48, and a first comparator 50. Logic signal processor 40 receives processed EMG signal 34 from high pass filter 30 and produces therefrom a switch control or logic signal 52.

EMG separating circuit 32 includes a first switch 54 having a control input connected to receive switch control signal 52 from first comparator 50. First switch 54 is configured to connect processed EMG signal 34 and first envelope processor 42 when switch control signal 52 is asserted and to isolate processed EMG signal 34 and first envelope processor 42 when the switch control signal 52 is deasserted.

As used herein, the terms "asserted" and "deasserted" correspond to a binary logic state of 1 and 0 for a positive logic convention and to a logic state of 0 and 1 for a negative logic convention, respectively. In the ensuing description, the terms "asserted" and "deasserted" are used in connection with a positive logic convention. However, this is not to be construed as limiting the present invention, which can also use a negative logic convention.

EMG separating circuit 32 also includes a second switch 56 having a control input connected to receive switch control signal 52 from first comparator 50. Second switch 56 is configured to connect first envelope processor 42 and moving average circuit 36 when switch control signal 52 is asserted and to isolate first envelope processor 42 and moving average circuit 36 when the switch control signal 52 is deasserted.

First envelope processor 42 includes a first high pass filter 58, which filters processed EMG signal 34 to produce therefrom a first high pass signal, which is supplied to a first full-wave rectifier 60. Preferably, first high pass filter 58 has a crossover frequency of about 24 Hz and an attenuation of approximately −24 db/octave. First full-wave rectifier 60 rectifies the first high pass signal to produce a first rectified signal that is supplied to a first low pass filter 62. First low pass filter 62 filters the first rectified signal to produce a first low pass or first envelope signal that is supplied to moving average circuit 36 through second switch 56. Preferably, first low pass filter 62 has a crossover frequency of about 16 Hz and an attenuation of approximately −6 db/octave.

Processed EMG signal 34 typically has voltage excursions above and below a ground or neutral reference. First high pass filter 58, first full-wave rectifier 60 and first low pass filter 62 of first envelope processor 42 coact to produce from processed EMG signal 34 a first envelope signal 61 having voltage excursions to one side of a ground or neutral reference G.

In the illustrated embodiment, second envelope processor 44 includes a second low pass filter 64 that filters processed EMG signal 34 from high pass filter 30. Second low pass filter 64 filters processed EMG signal 34 to produce a second low pass signal, which is supplied to a second full-wave rectifier 66. Preferably, second low pass filter 64 has a crossover frequency of approximately 16 Hz and an attenuation of approximately −6 db/octave. Second full-wave rectifier 66 rectifies the second low pass signal to produce a second rectified or second envelope signal. Second low pass filter 64 and second full-wave rectifier 66 of second envelope processor 44 coact to produce from processed EMG signal 34 a second envelope signal 67 having voltage excursions to one side of ground or a neutral reference G.

Fast signal processor 46 includes a third low pass filter 68 that filters the second rectified or second envelope signal from second full-wave rectifier 66 to produce a third low pass signal that is supplied to a first amplifier 70. Preferably, third low pass filter 68 has a crossover frequency of approximately 7 Hz and an attenuation of approximately −6 db/octave. First amplifier 70 amplifies the third low pass signal to produce a first amplified signal that is supplied to a fourth low pass filter 72. Preferably, first amplifier 70 has a gain less than unity and is biased to shift the level of the first amplified signal relative to a ground or neutral reference 100, shown best in FIG. 6B. Fourth low pass filter 72 filters the first amplified signal to produce a fourth low pass signal that is supplied to a combiner 74, which is also connected to receive the third low pass signal from third low pass filter 68. Preferably, fourth low pass filter 72 has a crossover frequency of approximately 0.16 Hz and an attenuation of approximately −12 db/octave. Combiner 74 combines the third low pass signal and the fourth low pass signal to produce a fast signal 76, perhaps shown best in FIG. 6B. More specifically, combiner 74 subtracts the fourth low pass signal from the third low pass signal to produce fast signal 76.

In the illustrated embodiment, first slow signal processor 48 includes a second amplifier 78 that receives second rectified or second envelope signal 67 from second full-wave rectifier 66. Second amplifier 78 amplifies the second rectified or second envelope signal to produce a second amplified signal that is provided to a fifth low pass filter 80. Preferably, second amplifier 78 has a gain greater than unity. In contrast to first amplifier 70, however, second amplifier 78 does not shift the level of the second amplified signal relative to a ground or a neutral reference 102, shown best in FIG. 6B. Fifth low pass filter 80 filters the second amplified signal to produce a first slow signal 82, shown best in FIG. 6B. Preferably, fifth low pass filter 80 has a crossover frequency of approximately 1.8 Hz and an attenuation of approximately −12 db/octave.

First comparator 50 includes a pair of inputs that receive fast signal 76 from fast signal processor 46 and first slow signal 82 from first slow signal processor 48. Preferably, first comparator 50 has an inverting input that receives fast signal 76 and a non-inverting input that receives first slow signal 82. Comparator 50 compares fast signal 76 and first slow signal 82 in a manner known in the art and produces, as a function of the comparison, switch control signal 52, which is asserted when first slow signal 82 is greater than fast signal 76, and which is deasserted when first slow signal 82 is less than fast signal 76.

Figures 6A, 6B, 6C:
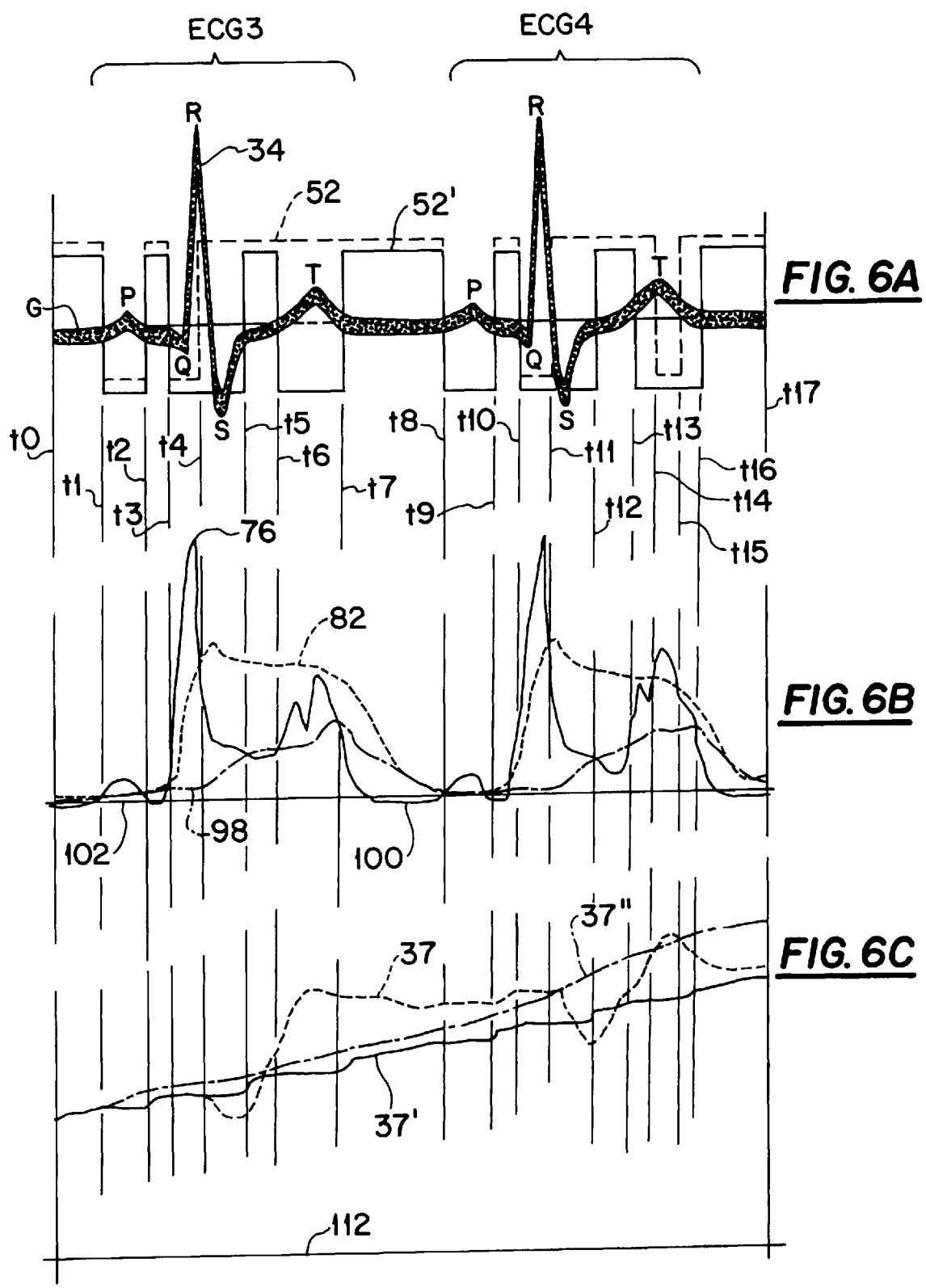
FIGS. 6A–6C are enlarged views of portions of the graphical illustrations of FIGS. 5A–5C, respectively, between times t0–t17.

EMG separating circuit 32 and moving average circuit 36 coact to produce model diaphragm EMG signal 37, shown best in FIG. 6C. The operation of EMG separating circuit 32 and moving average circuit 36 are described below following a description of an alternative embodiment of EMG separating circuit 32', which is shown in FIG. 4.

Figure 4:
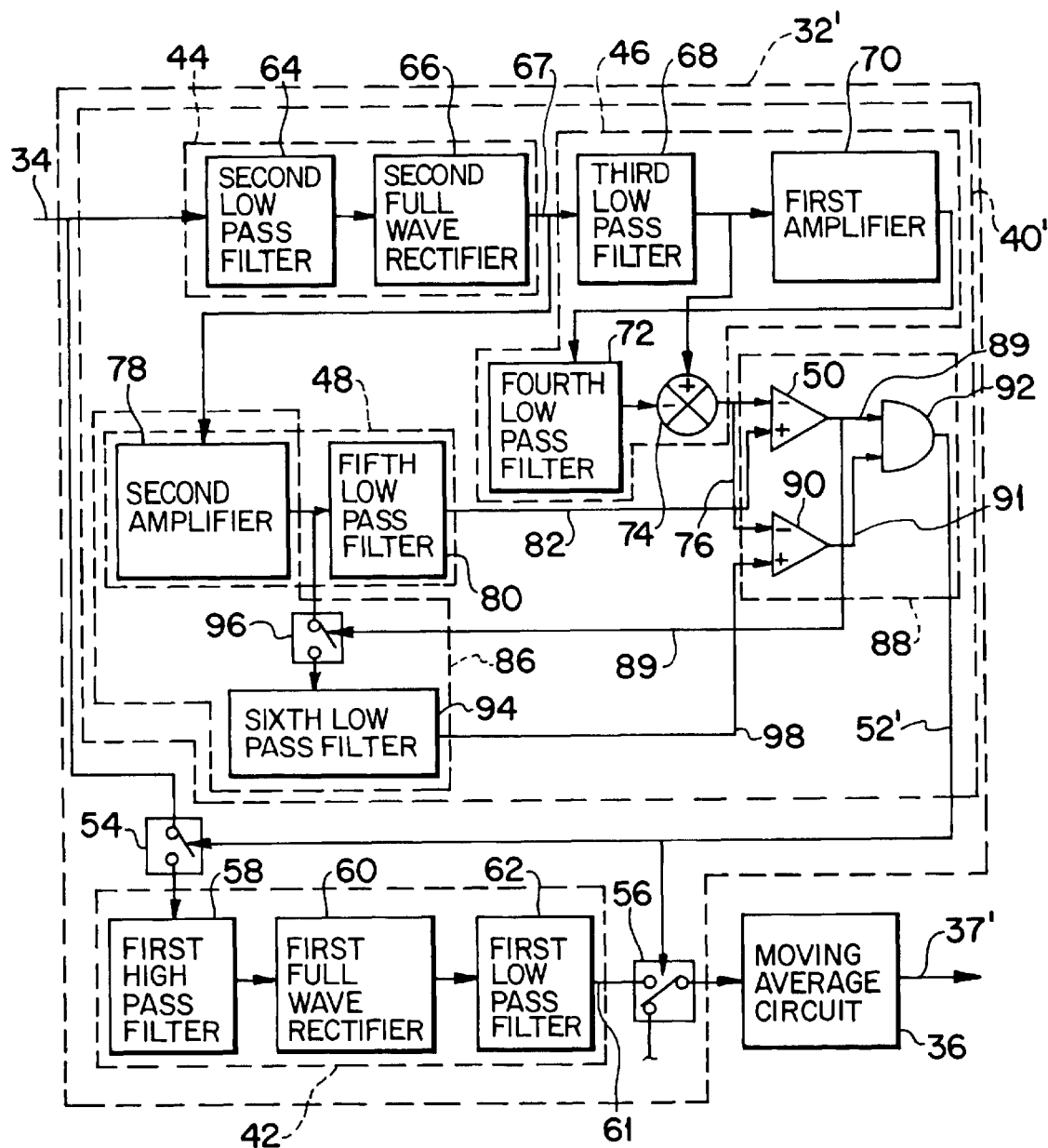
FIG. 4 is a schematic diagram of another embodiment of an EMG separating circuit of the EMG signal processing system shown in FIG. 2.

As shown in FIG. 4 and with continuing reference to all previous figures, another embodiment for an EMG separating circuit 32' includes first envelope processor 42 and a logic signal processor 40', which includes second envelope processor 44, fast signal processor 46, first slow signal processor 48 and first comparator 50. Logic signal processor 40' also includes a second slow signal processor 86 and a comparer 88. Comparer 88 includes first comparator 50, a second comparator 90 and a logic gate 92, preferably an AND gate. Second slow signal processor 86 includes a sixth low pass filter 94, which is configured to receive the second amplified signal from second amplifier 78, and a third switch 96 having a control input connected to the output of first comparator 50. Third switch 96 is configured to connect the second amplified signal to sixth low pass filter 94 when a first comparator signal produced at an output of first comparator 50 is asserted. Similarly, third switch 96 is configured to isolate the second amplified signal from sixth low pass filter 94 when the first comparator signal is deasserted. When the first comparator signal is asserted, sixth low pass filter 94 filters the second amplified signal to produce a second slow signal 98, shown best in FIG. 6B.

The first comparator 50 has as its inverting input, fast signal 76 from combiner 74 and has as its non-inverting input, first slow signal 82 from fifth low pass filter 80. Second comparator 90 has a non-inverting input connected to receive fast signal 76 from combiner 74 and a non-inverting input connected to receive second slow signal 98 from sixth low pass filter 94. First comparator 50 compares fast signal 76 and first slow signal 82 to produce a first comparator signal 89, which is asserted when first slow signal 82 is greater than fast signal 76, and which is deasserted when first slow signal 82 is less than a value of fast signal 76. Similarly, second comparator 90 produces on an output thereof a second comparator signal 91, which is asserted when second slow signal 98 is greater than fast signal 76 and which is deasserted when second slow signal 98 is less than fast signal 76. Logic gate 92 logically combines first comparator signal 89 and the second comparator signal 91 to produce a switch control or logic signal 52', which is supplied to first and second switches 54 and 56.

Preferably, switch control signal 52' is asserted when first and second comparator signals 89 and 91 are asserted and is deasserted when one or both of first and second comparator signals 89 and 91 are deasserted. EMG separating circuit 32' and the moving average circuit 36 coact to produce a model diaphragm EMG signal 37'.

Figure 5A:
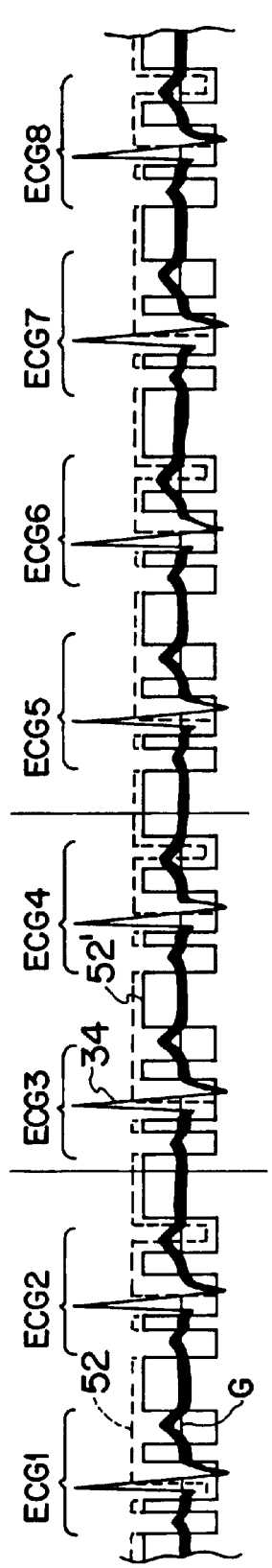
FIG. 5A is a graphical illustration of voltage versus time for a measured EMG signal and switch control signals produced by the EMG separating circuits of the present invention.
Figure 5B:
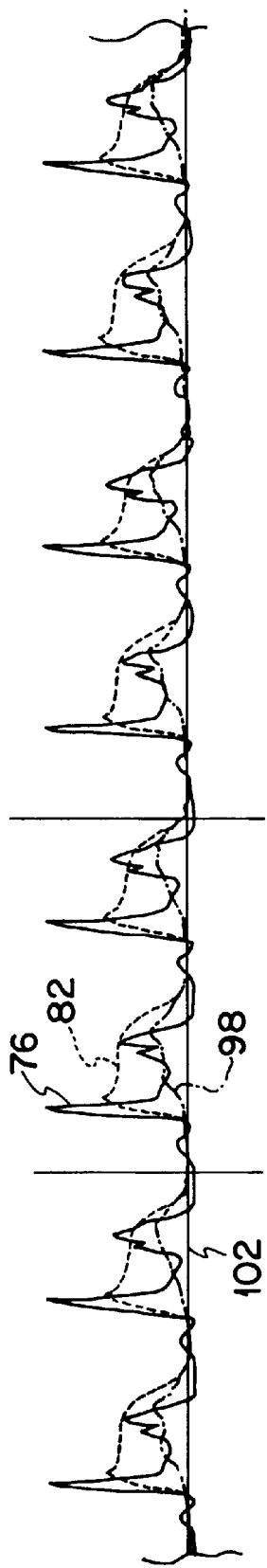
FIG. 5B is a graphical illustration of voltage versus time produced by a fast signal processor, a first slow signal processor, and a second slow signal processor of the present invention.

The operation of EMG separating circuit 32' is described hereafter with reference to FIGS. 5A–5C and 6A–6C, and with continuing reference to FIG. 4. As shown in FIG. 5A, processed EMG signal 34 received by EMG separating circuits 32' includes an electrocardiogram (ECG) signal having cycles ECG1–ECG8. In fact, processed EMG signal 34 is large dominated by the ECG signal. FIG. 5B shows fast signal 76, first slow signal 82, and second slow signal 98 generated by fast signal processor 46, first slow signal processor 48, and second slow signal processor 86, respectively, in response to based on processed EMG signal 34. In response to fast signal 76, first slow signal 82, and second slow signal 98, first and second comparators 50 and 90 and logic gate 92 of comparer 88 coact to produce on the output of logic gate 92 switch control signal 52', shown best in FIG. 5A, which controls switching of first and second switches 54 and 56. In response to controlling the switching of first and second switches 54 and 56, the first envelope processor 42 and the moving average circuit 36 coact to produce the model diaphragm EMG signal 37', shown best in FIG. 6C.

Figure 5C:
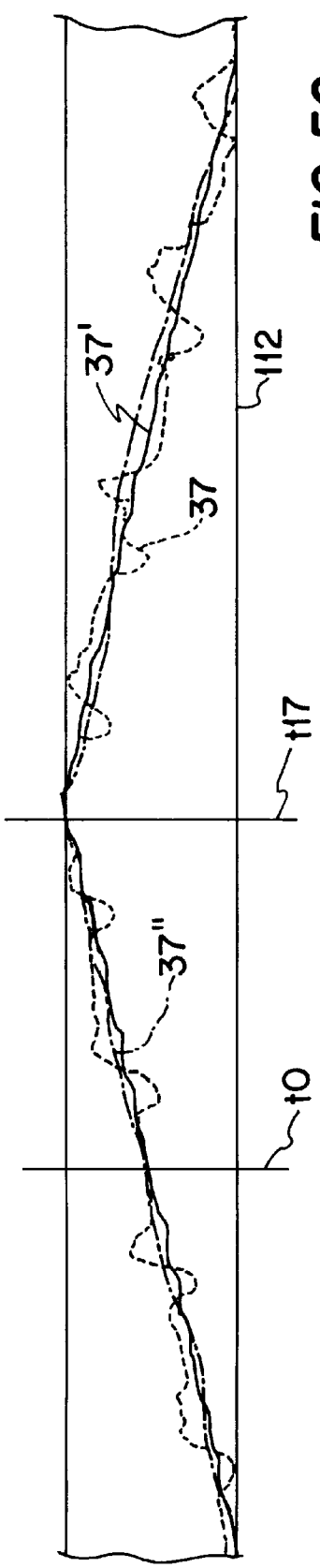
FIG. 5C is a graphical illustration of voltage versus time for model EMG signals produced in accordance with the present invention.

FIGS. 6A–6C show enlarged views of the signals shown in FIGS. 5A–5C, respectively, between times to and t17. FIG. 6A shows the ECG3 and the ECG4 cycles of processed EMG signal 34. The ECG3 and ECG4 cycles each include a P wave component, a QRS complex and a T wave component. As shown in FIG. 6B, fast signal 76 has a ground reference 100 which is shifted from, preferably below, ground reference 102 for first and second slow signals 82 and 98. As discussed above, first amplifier 70 produces this shift, which adjusts the interval during which first switch control signal 52' is asserted or deasserted.

Referring to FIGS. 4 and 6A–6C, between times t0 and t1, processed EMG signal 34 is relatively constant around ground reference G. In response to the relatively constant EMG signal between times t0 and t1, fast signal 76 is at its ground reference 100 and first and second slow signals 82 and 98 are at their ground reference 102. Because ground reference 100 is less than ground reference 102, first comparator signal 89 is asserted, second comparator signal 91 is asserted and switch control signal 52' is asserted. At time t1, adjacent a leading edge of the P wave of the ECG3 cycle, the processed EMG signal 34 increases in response to an increase in the P wave of the ECG3 cycle. Because fast signal processor 46 enables signals having a fast rate of change, or slew rate, to pass therethrough, fast signal 76 increases above the first and second slow signals 82 and 98. In response, first comparator signal 89, the second comparator signal 91 and switch control signal 52' change from asserted to deasserted at time t1.

When first comparator signal 89 changes from asserted to deasserted, third switch 96 opens, thereby isolating sixth low pass filter 94 from the second amplified signal produced by second amplifier 78. Moreover, in response to switch control signal 52' changing from asserted to deasserted, first and second switches 54 and 56 open, thereby isolating first envelope processor 42 from processed EMG signal 34 and moving average circuit 36.

At time t2, adjacent a trailing edge of the P wave of the ECG3 cycle, fast signal 76 decreases below first and second slow signals 82 and 98 in response to the P wave decreasing toward its ground reference G. In response, first and second comparator signals 89 and 91 change from deasserted to asserted and third switch 96 closes, thereby connecting sixth low pass filter 94 to receive the second amplified signal from second amplifier 78. Moreover, switch control signal 52' changes from deasserted to asserted, thereby causing first and second switches 54 and 56 to close and connect the first envelope processor 42 to processed EMG signal 34 and to connect moving average circuit 36 to first envelope signal 61 output from first envelope processor 42.

When the switch control signal 52' is asserted, first envelope processor 42 and the moving average circuit 36 coact to produce model diaphragm EMG signal 37', which varies as a function of the processed EMG signal 34. More specifically, when switch control signal 52' is asserted, moving average circuit 36 produces model diaphragm EMG signal 37' that varies as a function of a moving average of first envelope signal 61 produced by first envelope processor 42. In contrast, when the switch control signal 52' is deasserted, first envelope processor 42 is isolated from processed EMG signal 34 and moving average circuit 36. In response to being isolated from first envelope processor 42, moving average circuit 36 operates as a sample-and-hold to produce model diaphragm EMG signal 37' having a set value corresponding to a value of the moving average of the first envelope signal when switch control signal 52' changes from asserted to deasserted. Moreover, in response to isolation of first envelope processor 42 from processed EMG signal 34, first low pass filter 62 operates as a sample-and-hold to produce a set value for the first envelope signal. When switch control signal 52' changes from deasserted to asserted, first and second switches 54 and 56 close and connect first envelope processor 42 to processed EMG signal 34 and to connect first envelope signal 61 output from first envelope processor 42 to moving average circuit 36. In response, first envelope signal 61 initiates changing from its set value as a function of processed EMG signal 34, and moving average circuit 36 causes the model diaphragm EMG signal 37' to change as a function of the first envelope signal.

Logic signal processor 40' controls the state of switch control signal 52' so that when processed EMG signal 34 is changing rapidly due to the ECG signal and/or noise, first envelope signal 61 is not contributing to model diaphragm EMG signal 37'. In contrast, when processed EMG signal 34 is not changing rapidly due to the ECG signal and/or noise, model diaphragm EMG signal 37' varies as a function of first envelope signal 61 which varies as a function of processed EMG signal 34.

At time t3, adjacent a leading edge of the QRS complex, fast signal 76 increases above first and second slow signals 82 and 98 in response to a decrease of processed EMG signal 34. In response, first and second comparator signals 89 and 91 and switch control signal 52' change from asserted to deasserted. In response to the switch control signal 52' changing from asserted to deasserted, moving average circuit 36 generates model diaphragm EMG signal 37' having a set value which corresponds to the moving average of first envelope signal 61 when switch control signal 52' changes from asserted to deasserted.

In response to first comparator signal 89 changing from asserted to deasserted, third switch 96 opens and isolates sixth low pass filter 94 from the second amplified signal produced by second amplifier 78. In response, sixth low pass filter 94 operates as a sample-and-hold to produce second slow signal 98 having a set value corresponding to the value of second slow signal 98 when third switch 96 opens.

Between times t3 and t4, second slow signal 98 is at the set value and fast signal 76 and first slow signal 82 change in response to the Q wave and the R wave of the QRS complex of the ECG3 cycle. Because fast signal processor 46 enables fast signal 76 to change more rapidly than first slow signal 82 produced by first slow signal processor 48, the first slow signal 82 changes, e.g., increases, but to a lesser extent than fast signal 76 between times t3 and t4.

At time t4, fast signal 76 decreases below the increasing first slow signal 82. In response, first comparator signal 89 changes from deasserted to asserted and third switch 96 closes, thereby connecting sixth low pass filter 94 to receive the second amplified signal from second amplifier 78. In response to receiving the second amplified signal, sixth low pass filter 94 produces second slow signal 98 having a value that changes as a function of the second amplified signal. More specifically, when third switch 96 closes, second slow signal 98 initiates changing from the set value and begins converging toward first slow signal 82.

Because first slow signal 82 and second slow signal 98 diverged between times t3 and t4 and because fifth and sixth low pass filters 80 and 94 do not permit rapid changes of first slow signal 82 and second slow signal 98, respectively, second slow signal 98 converges gradually toward first slow signal 82.

In operation, fifth low pass filter 80 and sixth low pass filter 94 produce first slow signal 82 and second slow signal 98, respectively, having maximum slew rates that are less than the maximum slew rate of fast signal 76 produced by the fast signal processor 46. This difference in maximum slew rate enables fast signal 76 to change more rapidly than first and second slow signals 82 and 98 in response to second envelope signal 67. Hence, by appropriate selection of the characteristics of third, fourth, fifth and sixth low pass filters 68, 72, 80 and 94, i.e., crossover frequency and attenuation, the responses of fast signal 76 and first and second slow signals 82 and 98 can be adapted to cause first and second comparator signals 89 and 91 to change states at desired times of an ECG cycle of an EMG signal. For example, increasing the crossover frequency of fifth low pass filter 80 increases the maximum slew rate of first slow signal 82, thereby decreasing the interval during which first comparator signal 89 is deasserted after time t3. Similarly, decreasing the crossover frequency of fifth low pass filter 80 increases the interval during which first comparator signal 89 is deasserted after time t3. Similar comments apply with respect to sixth low pass filter 94 and second comparator signal 91. Moreover, adjusting the maximum slew rate of fast signal 76 by adjusting the crossover frequency of third and/or fourth low pass filters 68 and 72 adjusts the response of fast signal 76 with respect to first and second slow signals 82 and 98.

By suitable adjustment of the maximum slew rates of fast signal 76 and first and second slow signals 82 and 98, the state of switch control signal 52' can be adjusted as a function of processed EMG signal 34 and, more particularly, the ECG signal of processed EMG signal 34.

Between times t4 and t5, fast signal 76 decreases and second slow signal 98 increases in response to the R wave and the S wave of the ECG3 cycle. At time t5, adjacent a trailing edge of the QRS complex, fast signal 76 decreases below second slow signal 98 in response to the R wave decreasing toward the ground reference G. In response, second comparator signal 91 changes from deasserted to asserted. Because first comparator signal 89 is asserted, when second comparator signal 89 changes from deasserted to asserted at time t5, switch control signal 52' changes from deasserted to asserted.

Between times t5 and t6, fast signal 76 is less than first and second slow signals 82 and 98 and switch control signal 52' is asserted in response to processed EMG signal 34 being relatively constant around the ground reference G. In response to assertion of switch control signal 52', model diaphragm EMG signal 37' varies as a function of the moving average of first envelope signal 61.

At time t6, adjacent the leading edge of the T wave of the ECG3 cycle, fast signal 76 increases above second slow signal 98, which is gradually converging toward first slow signal 82, in response to the T wave of the ECG3 cycle increasing from the ground reference G. Between times t6 and t7, the T wave of the ECG3 cycle causes fast signal 76 to be greater than second slow signal 98, whereby second comparator signal 91 and switch control signal 52' are deasserted.

At time t7, the trailing edge of the T wave of the ECG3 cycle decreases to relatively constant around the ground reference G thereby causing fast signal 76 to converge toward its ground reference 100 and causing first and second slow signals 82 and 98 to converge toward their ground reference 102. Because it can react more rapidly than first and second slow signals 82 and 98, fast signal 76 converges toward its ground reference 100 more rapidly than first and second slow signals 82 and 98 converge toward their ground reference 102. Hence, between times t7 and t8, the value of fast signal 76 is below the values of first and second slow signals 82 or 98 and first and second comparator signals 89 and 91 and switch control signal 52' are asserted.

As discussed above, first comparator signal 89 changing from deasserted to asserted at time t4 causes second slow signal 98 to gradually converge toward first slow signal 82. This gradual convergence enables fast signal 76 between times t6 and t7 to be greater than second slow signal 98 and less than first slow signal 82. Hence, during the T wave of the ECG3 cycle, switch control signal 52' is deasserted due to fast signal 76 being greater than second slow signal 98.

At time t8, the leading edge of the P wave of the ECG4 cycle causes fast signal 76 to increase above first and second slow signals 82 and 98, whereby switch control signal 52' changes to deasserted. At time t9, the trailing edge of the P wave of the ECG4 cycle causes fast signal 76 to decrease below the values of first and second slow signals 82 and 98, whereby switch control signal 52' changes to asserted. At time t10, the leading edge of the QRS complex causes fast signal 76 to increase above first and second slow signals 82 and 98, whereby switch control signal 52' changes to deasserted.

Between times t10 and t11, fast signal 76 increases above first and second slow signals 82 and 98 in response to the Q wave and R wave of the ECG4 cycle. In response, first and second comparator signals 89 and 91 and the switch control signal 52' are deasserted and first, second, and third switches 54, 56 and 96 are opened. In response to third switch 96 opening, second slow signal 98 is a set value corresponding to the value thereof when first comparator signal 89 changes from asserted to deasserted. Similarly, in response to first and second switches 54 and 56 opening, model diaphragm EMG signal 37' is a set value corresponding to the value of the moving average of first envelope signal 61 when switch control signal 52' changes from asserted to deasserted.

At time t11, fast signal 76 decreases below first slow signal 82 in response to the trailing edge of the R wave of the ECG4 cycle. In response, first comparator signal 89 changes from deasserted to asserted, thereby causing third switch 96 to close. In response to closing third switch 96, second slow signal 98 initiates changing from the set value and begins gradually converging toward first slow signal 82.

Between times t11 and t12, the S wave of the ECG4 cycle causes fast signal 76 and second slow signal 98 to converge so that at time t12 fast signal 76 decreases below second slow signal 98, whereby second comparator signal 91 and the switch control signal 52' change to asserted.

At time t13, a leading edge of the T wave of the ECG4 cycle causes the value of fast signal 76 to increase above the value of second slow signal 98. In response, second comparator signal 91 and switch control signal 52' change to deasserted. At time t14, fast signal 76 increases above first slow signal 82 and first comparator signal 89 changes to deasserted, whereby third switch 96 opens and the value of second slow signal 98 is set at the value thereof when first comparator signal changed 89 to deasserted.

At time t15, fast signal 76 decreases below first slow signal 82 and first comparator signal 89 changes to deasserted, whereby third switch 96 connects sixth low pass filter 94 to receive the second amplified signal from second amplifier 78. In response, sixth low pass filter 94 causes the value of second slow signal 98 to initiate gradual changing from the set value toward first slow signal 82.

At time t16, the trailing edge of the T wave of the ECG4 cycle causes fast signal 76 to decrease below second slow signal 98. In response, second comparator signal 91 and switch control signal 52' change to asserted, thereby enabling model diaphragm EMG signal 37' to vary as a function of first envelope signal 61.

As shown in FIG. 6C, when switch control signal 52; in FIG. 6A is asserted, model diaphragm EMG signal 37' varies as a function of the moving average of first envelope signal 61. In contrast, when switch control signal 52' is deasserted, model diaphragm EMG signal 37' is a set value corresponding to the moving average of first envelope signal 61 when switch control signal 52' changes to deasserted.

If EMG separating circuit 32 shown in FIG. 3 is utilized, first comparator 50 produces switch control signal 52, shown in FIGS. 5A and 6A, to control switching of first and second switches 54 and 56. In FIGS. 5A and 6A, the value of switch control signal 52 is shifted upward from the value of switch control signal 52' for illustration purposes only. As shown in FIG. 6A, switch control signal 52 produced by EMG separating circuit 32 is asserted during portions of the S wave and/or the T wave of each ECG cycle when switch control signal 52' produced by EMG separating circuit 32' shown in FIG. 4 would be deasserted. Hence, while model diaphragm EMG signal 37 produced in response to operation of EMG separating circuit 32 of FIG. 3 has the same general shape as model diaphragm EMG signal 37' produced in response to operation of EMG separating circuit 32' of FIG. 4, model diaphragm EMG signal 37 includes more noise and ECG artifacts than model diaphragm EMG signal 37' generated by EMG separating circuit 32' of FIG. 4.

Yet another embodiment of an EMG separating circuit 32" is described below with reference to FIG. 7, and with continuing reference to FIGS. 5A–5C and 6A–6C. EMG separating circuit 32" includes logic signal processor 40' shown in FIG. 4, first envelope processor 42 shown in FIGS. 3 and 4, and a third envelope processor 104. Third envelope processor 104 includes a second high pass filter 106 connected to filter processed EMG signal 34 to produce a second high pass signal, which is provided to a third full-wave rectifier 108. Preferably, second high pass filter 106 has a crossover frequency of about 100 Hz and an attenuation of about −24 db/octave. Third full-wave rectifier 108 rectifies the second high pass signal and provides a third rectified signal to a seventh low pass filter 110. Seventh low pass filter 110 filters the third rectified signal to produce a seventh low pass or third envelope signal 111, which is provided to second switch 56. Preferably, seventh low pass filter 110 has a crossover frequency of about 16 Hz and an attenuation of about −6 db/octave. Second high pass filter 106, third full-wave rectifier 108, and seventh low pass filter 110 coact to produce from processed EMG signal 34, third envelope signal 111 having voltage excursions to one side of the ground or neutral reference G.

Figure 7:
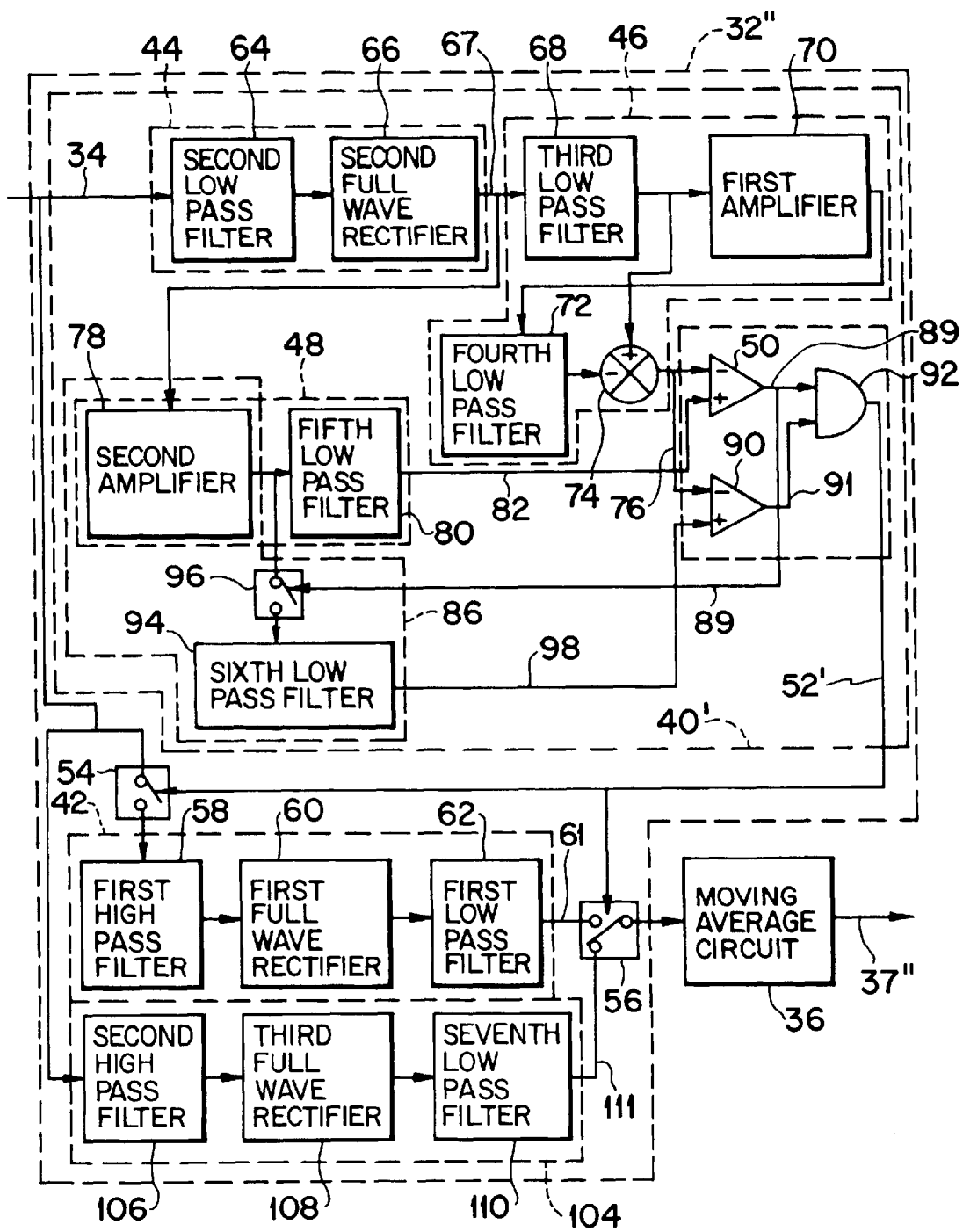
FIG. 7 is a schematic diagram of another embodiment of an EMG separating circuit of the EMG signal processing system shown in FIG. 2.

In the embodiment shown in FIG. 7, when switch control signal 52' is asserted, first and second switches 54 and 56 connect first envelope processor 42 to processed EMG signal 34 and moving average circuit 36. In contrast, when switch control signal 52' is deasserted, first envelope processor 42 is isolated from processed EMG signal 4 and moving average circuit 6, and third envelope processor 104 is connected to moving average circuit 36.

EMG separating circuit 32" causes moving average circuit 36 to produce a model diaphragm EMG signal 37", shown best in FIG. 6C, as a moving average of first envelope signal 61 when switch control signal 52' is asserted and as a function of third envelope signal 111 when switch control signal 52' is deasserted. Because it continuously processes processed EMG signal 34 via first envelope processor 42 or third envelope processor 104, moving average circuit 36 does not operate as a sample-and-hold when first envelope processor 42 is isolated therefrom, i.e., when switch control signal is deasserted. Hence, model diaphragm EMG signal 37" has a more continuous slope, with less stairstepping, i.e., relatively rapid variations, than model diaphragm EMG signals 37 and 37' produced by the EMG separating circuits 32 and 32' of FIGS. 3 and 4, respectively.

FIG. 5C shows model diaphragm EMG signals 37, 37' and 37" for one inhalation before time t17 and one exhalation after time t17. Between one exhalation and a subsequent inhalation (not shown), model diaphragm EMG signals 37, 37' and 37" are at a relatively steady state around a ground or neutral reference 112. In an exemplary embodiment of the present invention, ventilator 18 detects the slope of model diaphragm EMG signals 37, 37' or 37" received thereby and controls the supply of air to patient 2 as a function of the detected slope. For example, in response to detecting a positive slope of one of the model diaphragm EMG signals 37, 37' or 37'", ventilator 18 urges air into the lungs of patient 2. In response to detecting a negative slope or a relatively steady state value for the one of the model diaphragm EMG signals 37, 37' or 37", ventilator 18 terminates urging air into the lungs of the patient, enabling air to escape from the lungs due to relaxation of diaphragm 10 and the natural elastic properties of the thorax. It is to be understood that the present invention contemplates using model diaphragm EMG signals 37, 37' or 37" in any conventional manner to control a ventilator, and is not intended to be limited to the above description one exemplary embodiment of the to invention.

It can be appreciated from the foregoing that the present invention provides an apparatus and method for separating a model diaphragm EMG signal 37, 37', 37" from a measured EMG signal 17, which includes the patient's diaphragm signal, ECG signal, and other noise. Model diaphragm EMG signal 37, 37', 37" can be amplified to produce an amplified model diaphragm EMG signal 19, which can be used to control the operation of a respirator in a manner that avoids patient discomfort. The present invention provides a low cost, analog circuit that is capable of providing a model of a patient's diaphragm EMG signal simultaneously as it is being acquired. The circuit includes analog filtering, sensing the presence of and blocking of the P wave, QRS complex and T wave of an ECG cycle of the patient's EMG signal, full-wave rectifying of the remaining signal and creating its moving average with interpolation for the P wave, QRS complex and T wave of each ECG cycle.

It should be further noted that while the present invention has been described above as generating a model diaphragm EMG signal that is relatively noise-free, it is to be understood that the above-described processes can be used in conjunction with other EMG signals to produce model EMG signals that are relatively noise free. It is to be also understood that the above-described processes can be implemented in hardware or software or in a hardware/software combination and can be done using analog or digital signal processing or manipulation.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method of producing a model EMG signal from a measured EMG signal, wherein the measured EMG signal includes a patient's EMG signal and an ECG signal, the method comprising the steps of:
    (a) processing a measured EMG signal to produce a logic signal that is (1) in a first binary state responsive to an absence of a P wave, a QRS complex and a T wave in a measured EMG signal and (2) in a second binary state responsive to a presence of at least one of the P wave, the QRS complex, and the T wave in the measured EMG signal;
    (b) processing the measured EMG signal to produce a current first envelope signal; and
    (c) producing a model EMG signal as a function of (1) the current first envelope signal responsive to the logic signal being in the first binary state and (2) a signal other than the current first envelope signal responsive to the logic signal being in the second binary state.

2. The method as set forth in claim 1, wherein step (a) comprises:
    processing the measured EMG signal to produce a second envelope signal;
    processing the second envelope signal to produce a fast signal;
    processing the second envelope signal to produce a first slow signal having a slew rate slower than a slew rate of the fast signal; and
    processing the fast signal and the first slow signal to produce the logic signal.

3. The method as set forth in claim 1, wherein step (b) comprises the steps of:
    high pass filtering the measured EMG signal to produce a high pass signal;
    rectifying the first high pass signal to produce a rectified signal; and
    low pass filtering the rectified signal to produce the first envelope signal.

4. The method as set forth in claim 1, wherein step (c) comprises the steps of:
    providing, responsive to the logic signal being in the first binary state, a moving average of the current first envelope signal; and
    providing, responsive to the logic signal being in the second binary state, a set value that corresponds to a value of the moving average of the first envelope signal existing when the logic signal changed from the first binary state to the second binary state.

5. The method as set forth in claim 2, wherein the step of processing the measured EMG signal to produce the second envelope signal includes:
    low pass filtering the measured EMG signal to produce a first filtered signal, and
    rectifying the first filtered signal to produce the second envelope signal;
    wherein the step of processing the second envelope signal to produce the fast signal includes:
    low pass filtering the second envelope signal to produce a second filtered signal,
    amplifying the second filtered signal to produce a first amplified signal,
    low pass filtering the first amplified signal to produce a third filtered signal, and
    combining the second filtered signal and the third filtered signal to produce the fast signal;
    wherein the step of processing the second envelope signal to produce the first slow signal includes:
    amplifying the second envelope signal to produce a second amplified signal, and
    low pass filtering the second amplified signal to produce the first slow signal; and
    wherein the step of processing the fast signal and the first slow signal to produce the logic signal includes comparing the fast signal and the first slow signal to produce, as a function of the comparison, the logic signal.

6. The method as set forth in claim 2, further comprising:
    processing the second envelope signal to produce a second slow signal having a slew rate slower than the slew rate of the fast signal; and
    processing the fast signal, the first slow signal, and the second slow signal to produce the logic signal.

7. The method as set forth in claim 6, wherein the step of processing the fast signal, the first slow signal and the second slow signal to produce the logic signal includes:
    comparing the fast signal and the first slow signal to produce a first comparator signal;
    comparing the fast signal and the second slow signal to produce a second comparator signal; and
    combining the first comparator signal and the second comparator signal to produce the logic signal.

8. The method as set forth in claim 2, wherein step (b) includes continuously processing the EMG signal to produce a third envelope signal; and wherein step (c) includes:
    providing, responsive to the logic signal being in the first binary state, a moving average of the current first envelope signal, and providing, responsive to the logic signal being in the second binary state, a moving average of the third envelope signal.

9. The method as set forth in claim 8, wherein the step of processing the measured EMG signal to produce a first envelope signal includes:

high pass filtering the measured EMG signal to produce a first high pass signal, rectifying the first high pass signal to produce a first rectified signal, and low pass filtering the first rectified signal to produce the first envelope signal; and wherein the step of continuously processing the measured EMG signal to produce a third envelope signal includes:

high pass filtering the measured EMG signal to produce a second high pass signal, rectifying the second high pass signal to produce a second rectified signal, and low pass filtering the second rectified signal to produce the third envelope signal.

10. The method as set forth in claim 1, further including at least one of:

filtering the measured EMG signal prior to processing the measured EMG signal in at least one of steps (a) and (b); and amplifying the measured EMG signal prior to processing the measured EMG signal in at least one of steps (a) and (b).

11. An apparatus for producing a model EMG signal from a measured EMG signal, wherein the measured EMG signal includes a patient's EMG signal and an ECG signal, the apparatus comprising:

logic signal processing means for processing the measured EMG signal to produce a logic signal that is (1) in a first binary state responsive to an absence of a P wave, a QRS complex and a T wave in a measured EMG signal and (2) in a second binary state responsive to a presence of at least one of the P wave, the QRS complex, and the T wave in the measured EMG signal;

first envelope processing means for processing the measured EMG signal to produce a first envelope signal; and averaging means for producing a model EMG signal as a function of (1) the current first envelope signal responsive to the logic signal being in the first binary state and (2) a signal other than the current first envelope signal responsive to the logic signal being in the second binary state.

12. The apparatus as set forth in claim 11, wherein the logic signal processing means includes:

second envelope processing means for processing the measured EMG signal to produce a second envelope signal;

fast signal processing means for processing the second envelope signal to produce a fast signal;

first slow signal processing means for processing the second envelope signal to produce a first slow signal having a slew rate slower than a slew rate of the fast signal; and comparing means for comparing the fast signal and the first slow signal to produce the logic signal.

13. The apparatus as set forth in claim 11, wherein the first envelope processing means includes:

high pass filtering means for high pass filtering the measured EMG signal to produce a high pass signal, rectifying means for rectifying the high pass signal to produce a rectified signal, and low pass filtering means for low pass filtering the rectified signal to produce the first envelope signal.

14. The apparatus as set forth in claim 11, wherein the averaging means provides (1) a moving average of the current first envelope signal, responsive to the logic signal being in the first binary state and (2) a set value that corresponds to a value of the moving average of the first envelope signal existing when the logic signal changed from the first binary state to the second binary state, responsive to the logic signal being in the second binary state.

15. The apparatus as set forth in claim 12, wherein the second envelope processing means includes:

first low pass filtering means for low pass filtering the measured EMG signal to produce a first filtered signal, and first rectifying means for rectifying the first filtered signal to produce the second envelope signal;

the fast signal processing means includes:

second low pass filtering means for low pass filtering the second envelope signal to produce a second filtered signal, first amplifying means for amplifying the second filtered signal to produce a first amplified signal, third low pass filtering means for low pass filtering the first amplified signal to produce a third filtered signal, and combining means for combining the second filtered signal and the third filtered signal to produce the fast signal;

the first slow signal processing means includes:

second amplifying means for amplifying the second envelope signal to produce a second amplified signal, and fourth low pass filtering means for low pass filtering the second amplified signal to produce the first slow signal; and wherein the comparing means compares the fast signal and the first slow signal to produce, as a function of the comparison, the logic signal.

16. The apparatus as set forth in claim 12, wherein the logic signal processing means includes second slow signal processing means for processing the second envelope signal to produce a second slow signal having a slew rate slower than the slew rate of the fast signal, and wherein the comparing means produces the logic signal as a function of the fast signal, the first slow signal and the second slow signal.

17. The apparatus as set forth in claim 16, wherein the second envelope processing means includes:

first low pass filtering means for filtering the measured EMG signal to produce a first filtered signal, and first rectifying means for rectifying the first filtered signal to produce the second envelope signal;

the fast signal processing means includes:

second low pass filtering means for filtering the second envelope signal to produce a second filtered signal, first amplifying means for amplifying the second filtered signal to produce a first amplified signal, third low pass filtering means for filtering the first amplified signal to produce a third filtered signal, and combining means for combining the second filtered signal and the third filtered signal to produce the fast signal;

the first slow signal processing means includes:

second amplifying means for amplifying the second envelope signal to produce a second amplified signal, and fourth low pass filtering means for low pass filtering the second amplified signal to produce the first slow signal;

the second slow signal processing means includes:

the second amplifying means for amplifying the second envelope signal to produce the second amplified signal, and fifth low pass filtering means which low pass filters the second amplified signal to produce the second slow signal; and the comparing means includes:

first comparing means for comparing the fast signal and the first slow signal to produce a first comparator signal, second comparing means for compares the fast signal and the second slow signal to produce a second comparator signal, and logic gate means for combining the first comparator signal and the second comparator signal to produce the logic signal.

18. The apparatus as set forth in claim 11, further including at least one of:

filtering means for filtering the measured EMG signal prior to at least one of the logic signal processing means and the first envelope processing means processing the measured EMG signal; and amplifying means for amplifying the measured EMG signal prior to at least one of the logic signal processing means and the first envelope processing means processing the measured EMG signal.

19. The apparatus as set forth in claim 16, wherein the comparing means includes:

first comparing means for comparing the fast signal and the first slow signal to produce a first comparator signal;

second comparing means for comparing the fast signal and the second slow signal to produce a second comparator signal; and logic gate means for combining the first comparator signal and the second comparator signal to produce the logic signal.

20. The apparatus as set forth in claim 19, wherein the second slow signal processing means produces the second slow signal as a function of the second envelope signal responsive to the first comparator signal being in the first binary state and wherein the second slow signal processing means produces the second slow signal as a set value corresponding to a value of the second envelope signal existing when the first comparator signal changed from the first binary state to the second binary state responsive to the first comparator signal being in the second binary state.

21. The apparatus as set forth in claim 12, further including:

third envelope processing means for continuously processing the measured EMG signal to produce a third envelope signal, wherein the averaging means provides (1) a moving average of the first envelope signal responsive to the logic signal being in the first binary state and (2) a moving average of the third envelope signal responsive to the logic signal being in the second binary state.

22. The apparatus as set forth in claim 21, wherein:

the first envelope processing means includes:

first high pass filtering means for high pass filtering the measured EMG signal to produce a first high pass signal, first rectifying means for rectifying the first high pass signal to produce a first rectified signal, and first low pass filtering means for low pass filtering the first rectified signal to produce the first envelope signal; and the third envelope processing means includes:

second high pass filtering means for high pass filtering the measured EMG signal to produce a second high pass signal, second rectifying means for rectifying the second high pass signal to produce a second rectified signal, and second low pass filtering means for low pass filtering the second rectified signal to produce the third envelope signal.

23. An apparatus for producing a model EMG signal from a measured EMG signal, wherein the measured EMG signal includes a patient's EMG signal and ECG signal, the apparatus comprising:

a logic signal processor adapted to receive the measured EMG signal to produce a logic signal that is (1) in a first binary state responsive to an absence of a P wave, a QRS complex and a T wave in a measured EMG signal and (2) in a second binary state responsive to a presence of at least one of the P wave, the QRS complex, and the T wave in the measured EMG signal;

a first envelope processor adapted to receive such a measured EMG signal and output a first envelope signal based on the measured EMG signal;

an averager operatively coupled to the first envelope processor, wherein the averager outputs a signal corresponding to a moving average of the first envelope signal; and a switch system operatively coupled to the logic signal processor and to at least of the first envelope processor and the averager, wherein the switch system operates based on the logic signal to at least one of (1) communicate the measured EMG signal to the first envelope processor and (2) communicate the first envelope signal to the averager responsive to the logic signal being in the first binary state so that the averager provides the model EMG signal as a function of a current first envelope signal responsive to the logic signal being in the first binary state, and wherein the switch operates based on the logic signal to at least one of (3) prevent communication of the measured EMG signal to the first envelope processor and (4) prevent communication of the first envelope signal to the averager responsive to the logic signal being in the second binary state so that the averager provides the model EMG signal as a function of a signal other than the current first envelope signal responsive to the logic signal being in the second binary state.

24. The apparatus as set forth in claim 23, wherein the switching system includes:

a first switch that couples the measured EMG signal to the first envelope processor responsive to the logic signal being in the first binary state and isolates the measured EMG signal from the first envelope processor responsive to the logic signal being in the second binary state; and a second switch that couples the first envelope signal to the averager responsive to the logic signal being in the first binary state and isolates the first envelope signal from the averager responsive to the logic signal being in the second binary state.

25. The apparatus as set forth in claim 24, wherein the logic signal processor includes:

a second envelope processor adapted to receive such a measured EMG signal and output a second envelope signal based on the measured EMG signal;

a fast signal processor operatively coupled to the second envelope processor, wherein the fast signal processor outputs a fast signal based on the second envelope signal;

a first slow signal processor operatively coupled to the second envelope processor, wherein the first slow signal processor outputs a first slow signal based on the second envelope signal;

a comparer operatively coupled to the fast signal processor and the first slow signal processor, wherein the comparer compares the fast signal and the first slow signal to produce the logic signal.

26. The apparatus as set forth in claim 25, wherein the logic signal processor further comprises a second slow signal processor operatively coupled to the second envelope processor and the comparer, wherein the second slow signal processor outputs a second slow signal based on the second envelope signal, wherein the comparer produces the logic signal as a function of the fast signal, the first slow signal and the second slow signal.

27. The apparatus as set forth in claim 26, wherein the comparer includes:

a first comparator operatively coupled to the fast signal processor and the first slow signal processor, wherein the first comparator compares the fast signal and the first slow signal and outputs a first comparator signal based on this comparison;

a second comparator operatively coupled to the fast signal processor and the second slow signal processor, wherein the first comparator compares the fast signal and the second slow signal and outputs a second comparator signal based on this comparison; and a logic gate operatively coupled to the first comparator and the second comparator, wherein the logic gate logically combines the first comparator signal and the second comparator signal to produce the logic signal.

28. The apparatus as set forth in claim 27, wherein the second slow signal processor includes:

an amplifier operatively coupled to the second envelope processor, wherein the amplifier amplifies the second envelope signal and outputs an amplified signal;

a low pass filter operatively coupled to the amplifier, wherein the low pass filter low pass filters the amplified signal and outputs the second slow signal; and a third switch operatively coupled to the amplifier and the low pass filter, wherein the third switch couples the amplifier to the low pass filter responsive to the first comparator signal being in a first binary state and isolates the amplifier from the low pass filter responsive to the first comparator signal being in a second binary state, wherein the low pass filter produces the second slow signal as a function of (1) the amplified signal responsive to the first comparator signal being in the first binary state and (2) a set value corresponding to a value of the amplified signal existing when the logic signal changed from the first binary state to the second binary state responsive to the first comparator signal being in the second binary state.

29. The apparatus as set forth in claim 25, wherein:

the first envelope processor includes:

a first high pass filter adapted to receive such a measured EMG signal, wherein the first high pass filter high pass filters the measured EMG signal and outputs a first high pass signal, a first rectifier operatively coupled to the first high pass filter, wherein the first rectifier rectifies the first high pass signal and outputs a first rectified signal, and a first low pass operatively coupled to the first rectifier, wherein the first low pass filter low pass filters the first rectified signal and outputs the first envelope signal;

the second envelope processor includes:

a second low pass filter adapted to receive such a measured EMG signal, wherein the second low pass filter low pass filters the measured EMG signal and outputs a second low pass signal, a second rectifier operatively coupled to the second low pass filter, wherein the second rectifier rectifies the second low pass signal and outputs the second envelope signal;

the fast signal processor includes:

a third low pass filter operatively coupled to the second envelope processor, wherein the third low pass filter low pass filters the second envelope signal and outputs a third low pass signal, an amplifier operatively coupled to the third low pass filter, wherein the amplifier amplifies the third low pass filtered signal and outputs a first amplified signal, a fourth low pass operatively coupled to the amplifier, wherein the fourth low pass filter low pass filters the first amplified signal and outputs a fourth low pass signal, and a combiner operatively coupled to the third and the fourth low pass filters, wherein the combiner combines the third low pass signal and fourth low pass signal and outputs the fast signal; and the first slow signal processor includes:

a second amplifier operatively coupled to the second envelope processor, wherein the second amplifier amplifies the second envelope signal to produce the amplified signal and a fifth low pass filter which filters the amplified signal and outputs the first slow signal.

30. The apparatus as set forth in claim 23, further comprising a second envelope processor adapted to receive the measured EMG signal and output a second envelope signal based on the measured EMG signal, wherein the switch system communicates the measured EMG signal to the second envelope processor responsive to the logic signal being in the first binary state and prevents communication of the measured EMG signal to the second envelope processor and responsive to the logic signal being in the second binary state.

31. The apparatus as set forth in claim 23, further including a third envelope processor adapted to receive such a measured EMG signal, wherein the third envelope processor continuously processes the measured EMG signal and outputs a third envelope signal, and wherein the switch system couples the first envelope signal to the averager responsive to the logic signal being in the first binary state and couples the third envelope signal to the averager responsive to the logic signal is in the second binary state, with the averager producing the model EMG signal as a function of the first envelope signal responsive to the logic signal being in the first binary state and the third envelope signal responsive to the logic signal being in the second binary state.

32. The apparatus as set forth in claim 27, wherein at a leading edge of the P wave, the fast signal increases above the first and second slow signals, the first and second comparator signals change to deasserted, the second slow signal assumes the set value and the logic signal changes to the second binary state; and at a trailing edge of the P wave, the fast signal decreases below the first and second slow signals, the first and the second comparator signals change to asserted, the second slow signal initiates changing from the set value as a function of the amplified signal and the logic signal changes to the first binary state.

33. The apparatus as set forth in claim 27, wherein at a leading edge of the QRS complex, the fast signal increases above the first and second slow signals, the first and second comparator signals change from a first binary state to a second binary state, the second slow signal assumes the set value and the logic signal changes to the second binary state;

during the QRS complex, the fast signal decreases below the first slow signal, the first comparator signal changes to the first binary state and the second slow signal initiates changing from the set value as a function of the amplified signal whereby the second slow signal converges toward the first slow signal; and at a trailing edge of the QRS complex, the fast signal decreases below the second slow signal, the second comparator signal changes to the first binary state and the logic signal changes to the first binary state.

34. The apparatus as set forth in claim 27, wherein at a leading edge of the P wave, the fast signal increases above the second slow signal, the second comparator signal changes to the second binary state and the logic signal changes to the second binary state; and at a trailing edge of the P wave, the fast signal decreases below the second slow signal, the second comparator signal changes to the first binary state and the logic signal changes to the first binary state.

35. The apparatus as set forth in claim 23, further including at least one of:

a filter adapted to receive the measured EMG signal and operatively coupled to at least one of the first envelope processor and the logic signal processor, wherein the filter filters the measured EMG signal prior to at least one of the first envelope processor and the logic signal processor processing the measured EMG signal; and an amplifier adapted to receive the measured EMG signal and operatively coupled to at least one of the first envelope processor and the logic signal processor, wherein the amplifier amplifies the measured EMG signal prior to at least one of the first envelope processor and the logic signal processor processing the measured EMG signal.

36. The apparatus as set forth in claim 23, further comprising a pair of sensors adapted to be coupled to a patient to output the measured EMG signal.

* * * * *